United States Patent
Kadobayashi

(10) Patent No.: US 8,758,014 B2
(45) Date of Patent: Jun. 24, 2014

(54) ARTIFICIAL TEETH

(71) Applicant: Kabushiki Kaisha Shofu, Kyoto (JP)

(72) Inventor: Yusei Kadobayashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 14/078,597

(22) Filed: Nov. 13, 2013

(65) Prior Publication Data

US 2014/0072933 A1    Mar. 13, 2014

Related U.S. Application Data

(63) Continuation of application No. 12/461,100, filed on Jul. 31, 2009.

(30) Foreign Application Priority Data

Aug. 1, 2008  (JP) .................................. 2008-199291
Jul. 29, 2009 (JP) .................................. 2009-176728

(51) Int. Cl.
*A61C 13/10* (2006.01)

(52) U.S. Cl.
USPC ........................................................ 433/191

(58) Field of Classification Search
USPC .................................. 433/191, 192, 196, 197
See application file for complete search history.

(56) References Cited

U.S. PATENT DOCUMENTS

| | | | |
|---|---|---|---|
| 2,300,577 | A | 11/1942 | La Due et al. |
| 5,733,125 | A | 3/1998 | Foser |
| 6,533,581 | B1 | 3/2003 | Moenckmeyer |
| 7,267,549 | B2 | 9/2007 | Monkmeyer |
| 2005/0095559 | A1 | 5/2005 | Monkmeyer |

FOREIGN PATENT DOCUMENTS

| | | |
|---|---|---|
| JP | 2002-177301 | 6/2002 |
| JP | 2002-523134 | 7/2002 |
| JP | 2005-525841 | 9/2005 |
| JP | 2006-042954 | 2/2006 |

OTHER PUBLICATIONS

Notification of Reason for Refusal issued Feb. 9, 2010 (with English translation) in a Japanese application that is a foreign counterpart to the present application.

*Primary Examiner* — Sunil K Singh
(74) *Attorney, Agent, or Firm* — Wenderoth, Lind & Ponack, L.L.P.

(57) ABSTRACT

The invention enables artificial molar teeth to be arranged at appropriate positions according to the oral cavity environment of each patient without requiring advanced techniques or experience. The artificial molar teeth have maxillary molar teeth and mandibular molar teeth arranged so as to form a pair on denture bases to be mounted on upper and lower jaws in an oral cavity, in which one cusp out of the cusps of the maxillary molar teeth and the mandibular molar teeth is engaged with a fossa of the antagonist, and at least one of the other cusps is engaged with a groove of the antagonist.

12 Claims, 3 Drawing Sheets

ARTIFICIAL TEETH

BACKGROUND OF THE INVENTION

I. Field of the Invention

The present invention relates to artificial molar teeth capable of easy arrangement when making a dental prosthetic appliance, and easy chewing at the time of mounting it as dentures.

II. Description of Related Art

Arrangement of artificial molar teeth when making a dental prosthetic appliance demands advanced techniques and experience. It has been particularly difficult to arrange opposed teeth in a proper position relative to each other. In conventional artificial teeth, the relation of cusps and fossae of the teeth has been considered to be important, and it has been desirable to make a stable shape so that it is possible for each of a plurality of cusps to engage with the fossae. Further, it has been desirable to develop artificial teeth which do not require much grinding after arrangement or large changing of the surface state.

Japanese Patent Application Laid-Open No. 2002-177301 discloses artificial molar teeth in which a lingual cusp, a buccal cusp, and a fossa are formed on the occlusal surface of maxillary molar teeth, and also a lingual cusp, a buccal cusp, and a fossa are formed on the occlusal surface of antagonist, i.e. opposed mandibular molar teeth. These artificial molar teeth are configured such that at a central occlusal position the lingual cusp of the maxillary molar teeth occludes and contacts with the fossa of the mandibular antagonist, and the buccal cusp of the mandibular antagonist occludes and contacts with the fossa of the maxillary molar teeth.

In the artificial molar teeth disclosed in Japanese Patent Application Laid-Open No. 2002-177301, occlusal contact occurs in a total of 18 points, 9 points at the left and 9 points at the right. In other words, the number of occlusal contact points is smaller than in the full-balanced occlusion, and there is no occlusal contact with the inclined surface of the buccal cusp as in the full-balanced occlusion. Accordingly, when making dentures, arrangement on the wax alveolar ridge or occlusal adjustment by grinding or the like is easy. When the dentures are used, the dentures are stable without falling over. In mastication efficiency including grinding, biting and cutting of food, a satisfactory occlusion close to the full-balanced occlusion will be obtained. Moreover, changing to a lingualized occlusion can be easily conducted not only when making dentures but also when correcting the dentures.

However, in the artificial molar teeth disclosed in Japanese Patent Application Laid-Open No. 2002-177301, it is required to achieve occlusal contacts between the lingual cusp of maxillary molar teeth and the fossa of mandibular antagonist, and between the fossa of maxillary molar teeth and the buccal cusp of mandibular antagonist, respectively. Therefore, it has been extremely difficult to make dentures for each patient according to the complicated oral cavity environments of patients. Besides, the cusp of the artificial molar teeth may be distorted in a molding process. Therefore, it is extremely difficult to mold the cusp in a shape exactly engaging with the fossae of the antagonist, causing the disadvantage of poor yield ratio.

Japanese Patent Application Laid-Open No. 2006-42954 discloses an occlusion adjusting method in which cavities of a specified depth are provided on the occlusal surface of mandibular artificial teeth configuring dentures, and the cavities are filled with a plastic dental material of resin or an inlay wax of casing.

In Japanese Patent Application Laid-Open No. 2006-42954, in a state where the upper and lower dentures are occluded, by moving the lower jaw to the moving limits from front to back and side to side, the track of the lingual cuspal tops of the maxillary molar teeth contacting and passing on the occlusal surface of the mandibular molar teeth is recorded as a sliding and contacting trace on the surface of the plastic dental material or the inlay wax. By grinding this sliding and contacting trace according to a common dental method, the state of occlusion can be adjusted.

However, in the artificial molar teeth of Japanese Patent Application Laid-Open No. 2006-42954, the cuspal portion of the occlusal surface side and the tooth root portion of the root side need to be formed in different molds, and it is necessary to adjust occlusion by taking the motion of jaw in an oral cavity. Therefore, the making process of the dentures is long and complicated, and the burden to a patient was significant.

SUMMARY OF THE INVENTION

It is an object of the invention to provide artificial molar teeth that can be arranged at proper positions according to the oral cavity environment of each patient without requiring advanced techniques or experience.

In order to achieve the object, the artificial molar teeth of the invention have maxillary molar teeth and mandibular molar teeth to be arranged so as to form a pair on denture bases to be mounted on upper and lower jaws in an oral cavity, in which one cusp out of cusps of the maxillary molar teeth and the mandibular molar teeth is engaged with a fossa of the antagonist, and at least one of the other cusps is engaged with a groove of the antagonist.

Specifically, it is configured that the artificial molar teeth have maxillary molar teeth and mandibular molar teeth to be arranged so as to form a pair on denture bases to be mounted on upper and lower jaws in an oral cavity, the lingual cusp of the maxillary molar teeth contacting with the mandibular molar teeth, and the buccal cusp of the mandibular molar teeth contacting with the maxillary molar teeth, in which one cusp out of cusps of the maxillary molar teeth and the mandibular molar teeth is engaged with a fossa of the antagonist, and at least one of the other cusps is engaged with a groove of the antagonist.

In the artificial molar teeth, preferably, a pair of lingual cusps are provided in the maxillary molar teeth, and a pair of buccal cusps are provided in the mandibular molar teeth.

The cusp to be engaged with the fossa is preferred to be a crushing cusp.

The other cusps except for the cusp engaged with the fossa and the cusp engaged with the groove are desired to be configured so as to contact with the bulged portions of the antagonist.

In the artificial molar teeth of the invention, in a state that one cusp out of the cusps of the maxillary molar teeth and the mandibular molar teeth is engaged with the fossa of antagonist, the tooth is rotated for fine adjustment so that the other cusps can be easily engaged with the groove of the antagonist, and can be adjusted to specified positions and arranged. Therefore, when arranging the individual artificial molar teeth, high precision is not needed in the arrangement positions. Hence, when arranging the teeth according to the oral cavity environment of a patient at the time of making teeth, the upper and lower teeth can be arranged at specified positions without requiring advanced techniques or experience. When molding the artificial molar teeth, advanced precision is not required, and the artificial molar teeth can be arranged even if the teeth have some deformation. As a result, the manufacturing cost of the artificial molar teeth can be significantly decreased.

BRIEF DESCRIPTION OF THE DRAWINGS

FIG. 3 (B) is a plan view showing an engaged state of molar teeth.

DETAILED DESCRIPTION OF THE INVENTION

The embodiments of the invention are specifically described below with reference to drawings.

The invention is a technique for making artificial teeth as dental prosthetic appliances being dentures, and more particularly is a technique capable of applying for making of artificial molar teeth. The artificial molar teeth include a first molar tooth, a second molar tooth, a first premolar tooth, and a second premolar tooth, and in particular a combination of at least a pair of upper and lower opposed teeth is preferred, and more preferably a combination of four upper and lower artificial teeth including the first molar tooth, the second molar tooth, the first premolar tooth, and the second premolar tooth.

Figure 1:
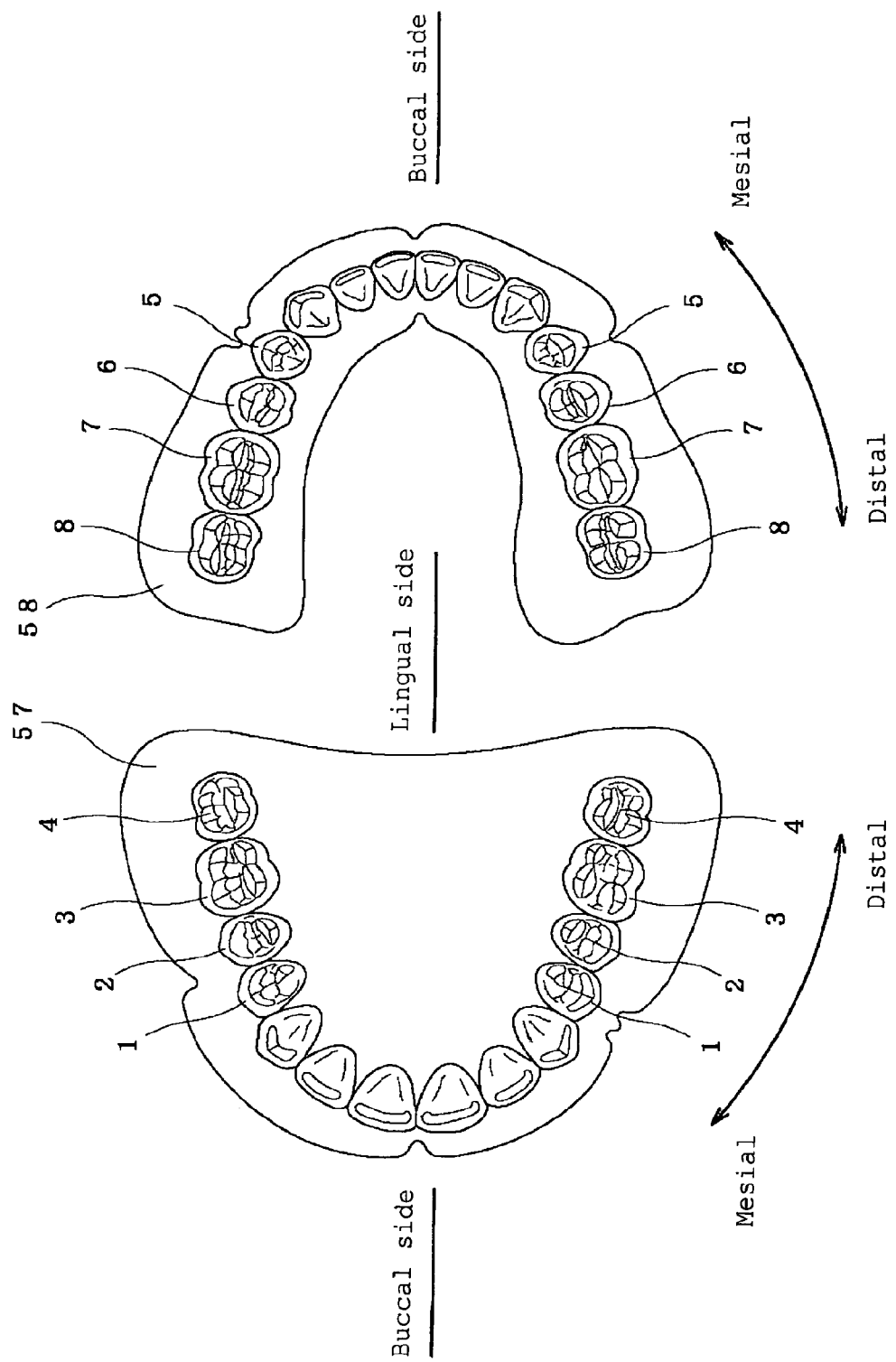
FIG. 1 is a plan view showing a basic configuration of artificial teeth disposed in an upper jaw and a lower jaw.

FIG. 1 shows an arrangement of all artificial teeth, showing an upper jaw at left and a lower jaw at right. In the artificial teeth, one tooth of the upper jaw corresponds to one tooth of the lower jaw. In the following description, a direction approaching to anterior teeth is referred to as a mesial side, and a direction departing therefrom as a distal side. The inside of an oral cavity is referred to as a lingual side, and the outside of an oral cavity as a buccal side.

First, the basic configuration of artificial molar teeth will be described. As shown in FIG. 1, the artificial molar teeth include a maxillary first molar tooth 1, a maxillary second molar tooth 2, a maxillary first premolar tooth 3, and a maxillary second premolar tooth 4 arranged in an upper jaw, and a mandibular first molar tooth 5, a mandibular second molar tooth 6, a mandibular first premolar tooth 7, and a mandibular second premolar tooth 8 arranged in an opposed lower jaw. These teeth 1 to 8 are opposed, in order from the mesial side, as a pair (cusp to fossa) of the maxillary first premolar tooth 1 and the mandibular first premolar tooth 5, a pair of the maxillary second premolar tooth 2 and the mandibular second premolar tooth 6, a pair of the maxillary first molar tooth 3 and the mandibular first molar tooth 7, and a pair of the maxillary second molar tooth 4 and the mandibular second molar tooth 8.

Figure 2:
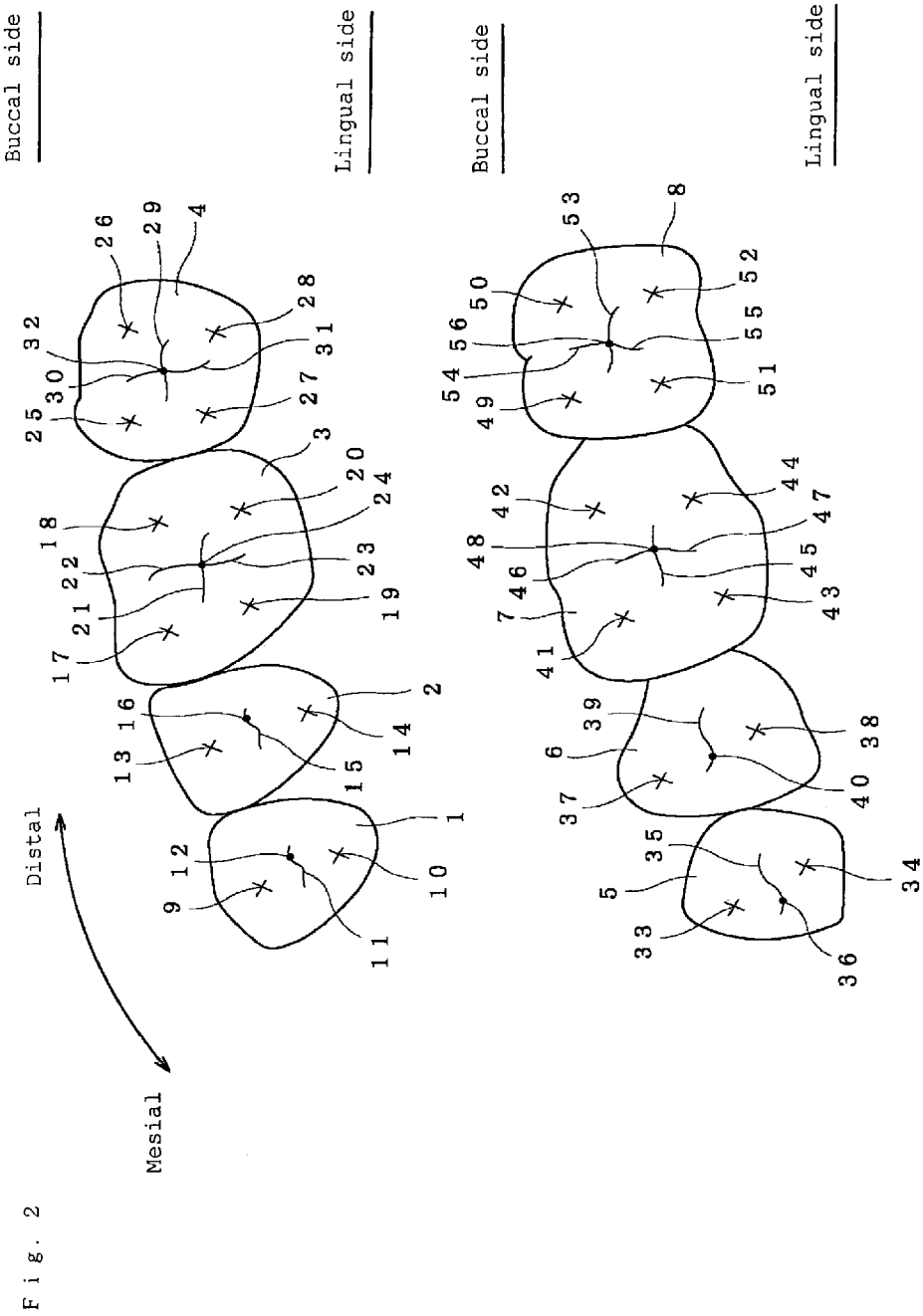
FIG. 2 is a conceptual diagram showing an state of the maxillary molar teeth and the mandibular molar teeth of the invention arranged and placed in the upper and lower positions, respectively.

As indicated by the x-mark in FIG. 2, the maxillary first premolar tooth 1 is provided with a buccal cusp 9 at the buccal side, and a lingual cusp 10 at the lingual side. These cusps 9, 10 have a shape in which a bulky tooth substance bulges in a tapered form. The maxillary first premolar tooth 1 is provided with a central groove 11 extending toward the mesial and distal directions between the buccal cusp 9 and the lingual cusp 10. On this central groove 11, a fossa 12 of the greatest depth in the vertical direction in an arranged state is formed at a specified position.

The maxillary second premolar tooth 2 is provided with a buccal cusp 13 at the buccal side, and a lingual cusp 14 at the lingual side. These cusps 13, 14 have a shape in which a bulky tooth substance bulges in a tapered form. The maxillary second premolar tooth 2 is provided with a central groove 15 extending toward the mesial and distal directions between the buccal cusp 13 and the lingual cusp 14. On this central groove 15, a fossa 16 is formed at a specified position.

The maxillary first molar tooth 3 is provided with a mesial buccal cusp 17 at the mesial side of the buccal side, a distal buccal cusp 18 at the distal side of the buccal side, a mesial lingual cusp 19 at the mesial side of the lingual side, and a distal lingual cusp 20 at the distal side of the lingual side. These cusps 17 to 20 have a shape in which a bulky tooth substance bulges in a tapered form. Of these cusps 17 to 20, the distal lingual cusp 20 is a crushing cusp mainly acting when grinding, biting or cutting the food. The maxillary first molar tooth 3 is provided with a central groove 21 extending toward the mesial and distal directions between each pair of the buccal cusps 17, 18 and lingual cusps 19, 20. A buccal side groove 22 and a lingual side groove 23 extending toward the buccal side and lingual side are formed between each pair of the mesial cusps 17, 19 and distal cusps 18, 20. A fossa 24 is formed at the intersecting portion of the grooves 21 to 23.

The maxillary second molar tooth 4 is provided with a mesial buccal cusp 25 at the mesial side of the buccal side, a distal buccal cusp 26 at the distal side of the buccal side, a mesial lingual cusp 27 at the mesial side of the lingual side, and a distal lingual cusp 28 at the distal side of the lingual side. These cusps 25 to 28 have a shape in which a bulky tooth substance bulges in a tapered form. The maxillary second molar tooth 4 is provided with a central groove 29 extending toward the mesial and distal directions between each pair of the buccal cusps 25, 26 and lingual cusps 27, 28. A buccal side groove 30 and a lingual side groove 31 extending toward the buccal side and lingual side are formed between each pair of the mesial cusps 25, 27 and distal cusps 26, 28. A fossa 32 is formed at the intersecting portion of the grooves 29 to 31.

On the other hand, the mandibular first premolar tooth 5 is provided with a buccal cusp 33 at the buccal side, and a lingual cusp 34 at the lingual side. These cusps 33, 34 have a shape in which a bulky tooth substance bulges in a tapered form. The mandibular first premolar tooth 5 is provided with a central groove 35 extending toward the mesial and distal directions between the buccal cusp 33 and lingual cusp 34. On this central groove 35, a fossa 36 is formed at a specified position.

The mandibular second premolar tooth 6 is provided with a buccal cusp 37 at the buccal side, and a lingual cusp 38 at the lingual side. These cusps 37, 38 have a shape in which a bulky tooth substance bulges in a tapered form. The mandibular second premolar tooth 6 is provided with a central groove 39 extending toward the mesial and distal directions between the buccal cusp 37 and lingual cusp 38. On this central groove 39, a fossa 40 is formed at a specified position.

The mandibular first molar tooth 7 is provided with a mesial buccal cusp 41 at the mesial side of the buccal side, a distal buccal cusp 42 at the distal side of the buccal side, a mesial lingual cusp 43 at the mesial side of the lingual side, and a distal lingual cusp 44 at the distal side of the lingual side. These cusps 41 to 44 have a shape in which a bulky tooth substance bulges in a tapered form. The mandibular first molar tooth 7 is provided with a central groove 45 extending toward the mesial and distal directions between each pair of the buccal cusps 41, 42 and lingual cusps 43, 44. A buccal side groove 46 and a lingual side groove 47 extending toward the buccal side and lingual side are formed between each pair of the mesial cusps 41, 43 and distal cusps 42, 44. A fossa 48 is formed at the intersecting portion of the grooves 45 to 47.

The mandibular second molar tooth 8 is provided with a mesial buccal cusp 49 at the mesial side of the buccal side, a distal buccal cusp 50 at the distal side of the buccal side, a mesial lingual cusp 51 at the mesial side of the lingual side, and a distal lingual cusp 52 at the distal side of the lingual side. The mandibular second molar tooth 8 may be provided with another cusp at the distal side. These cusps 49 to 52 have a shape in which a bulky tooth substance bulges in a tapered form. The mandibular second molar tooth 8 is provided with a central groove 53 extending toward the mesial and distal directions between each pair of the buccal cusps 49, 50 and lingual cusps 51, 52. A buccal side groove 54 and a lingual side groove 55 extending toward the buccal side and lingual side are formed between each pair of the mesial cusps 49, 51 and distal cusps 50, 52. A fossa 56 is formed at the intersecting portion of the grooves 53 to 55.

The maxillary molar teeth 1 to 4 are arranged in a maxillary base 57, and the mandibular molar teeth 5 to 8 are arranged in a mandibular base 58. Byway of the maxillary base 57 and mandibular base 58, the teeth are detachably mounted in the oral cavity of a patient. The mandibular base 58 is formed in a nearly U-shape for allowing to expose the patient's tongue.

In the embodiment, in these artificial molar teeth 1 to 8, of the upper and lower pairs of teeth 1, 5 to 4, 8, the cusp of one tooth of 1 to 4, 5 to 8 is configured to fall into (engaged with) the fossa of the antagonist of 5 to 8, 1 to 4. Of the artificial molar teeth 1 to 4, 5 to 8, one of the other cusps excluding the cusp to be engaged with the fossa is configured to be engaged with a groove in the antagonist of 5 to 8, 1 to 4. Pairing teeth 1, 5 to 4, 8 are further provided with another cusps, except for the cusp to be engaged with the fossa and the cusp to be engaged with the groove. That is, in a closed state at a central occlusal position, the maxillary molar teeth 1 to 4 have buccal cusps 17, 18, 25, 26, and the mandibular molar teeth 5 to 8 have lingual cusps 43, 44, 51, 52. These cusps are configured not to be engaged with any one of the antagonist 1 to 4, 5 to 8. The molar teeth 3, 4, 7, 8 are further provided with another cusps, except for the cusp engaged with the fossa, the cusp engaged with the groove, and the cusp not engaged with anything. The other cusp is configured to contact with the bulged portion of the antagonist 7, 8, 3, 4.

Specifically, in the case of the molar teeth 3, 4, 7, 8, the maxillary first motor tooth 3 and the mandibular first motor tooth 7, and the maxillary second motor tooth 4 and the mandibular second motor tooth 8 contact with each other in a total of four cusps. In the maxillary molar teeth 3, 4, such cusps are the lingual cusps 19, 20, 27, 28, and in the mandibular molar teeth 7, 8, such cusps are the buccal cusps 41, 42, 49, 50. In the case of the first molar teeth 3, 7, one of the lingual cusps 19, 20 of the maxillary first molar tooth 3 and the buccal cups 41, 42 of the mandibular first molar tooth 7 is engaged with the fossae 24, 48 of the antagonist. In the case of the second molar teeth 4, 8, one of the lingual cusps 27, 28 of the maxillary second molar tooth 4 and the buccal cups 49, 50 of the mandibular second molar tooth 8 is configured to be engaged with the opposed fossae 32, 56. Further, the cusp adjacent to the same side of the cusp engaged with the groove is engaged with the opposed groove. In the case of premolar teeth 1, 2, 5, 6, in an engagement between the maxillary premolar teeth 1, 2 and the mandibular premolar teeth 5, 6, one of the cusps 10, 11, 13, 14 of each of the maxillary premolar teeth 1, 2, and one of the cusps 33, 34, 37, 38 of each of the mandibular premolar teeth 5, 6 contact with the antagonist, respectively. Accordingly, in the case of the first premolar teeth 1, 5, one of the lingual cusp 10 of the maxillary first premolar tooth 1 and the buccal cusp 33 of the mandibular first premolar tooth 5 is engaged with the fossae 12, 36 of the antagonist, and the other is engaged with the grooves 11, 35. In the case of the second premolar teeth 2, 6, one of the lingual cusp 14 of the maxillary second premolar tooth 2 and the buccal cusp 37 of the mandibular second premolar tooth 6 is engaged with the opposed fossae 16, 40, and the other is engaged with the grooves 15, 39. In the embodiment, one cusp of maxillary molar teeth 1 to 4 is configured to fall into the fossae 36, 40, 48, 56 of the mandibular molar teeth 5 to 8.

Herein, an engagement with a fossa includes a configuration in which the top portion of a cusp contacts with the bottom of a fossa, and a configuration in which the bulged portion of a cusp abuts on the periphery of the fossa (the inner wall of the groove), without contacting of the top of the cusp with the bottom of a fossa. That is, it means a state where the cusp top is engaged with the fossa even if the cusp top is not contacting with the antagonist. In other words, at the engagement with a fossa means a state where the position of the cusp is fixed and does not move even if the other portion is not contacting. An engagement with a groove means a state where the cusp is movable along the groove and is not fixed in a position when the other portion is not engaged. In this way, it is configured such that the position of the cusp is determined by engagement with the fossa, and the position of the maxillary molar teeth 1 to 4 and the mandibular molar teeth 5 to 8 is determined in the other groove according to this position. The groove is constituted with a valley between fossae or bulged portions. The engagement with a groove includes an engagement with a valley, and is preferably an engagement with a valley. An engagement with a valley means a state where the cusp of the antagonist does not contact with the groove, but contacts with two positions of the bulged portion configuring the groove.

A specific aspect of the embodiment will be described below. The following description is carried out by way of the second premolar teeth 2, 6 and the first molar teeth 3, 7, but the same applies also to the first premolar teeth 1, 5 and the second molar teeth 4, 8.

Figure 3:
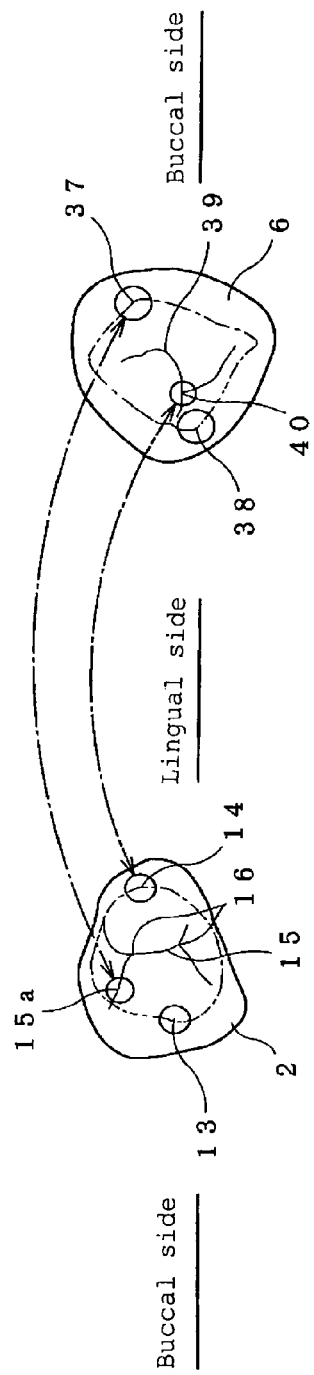
FIG. 3 (A) is a plan view showing an engaged state of premolar teeth.
Figure 3:
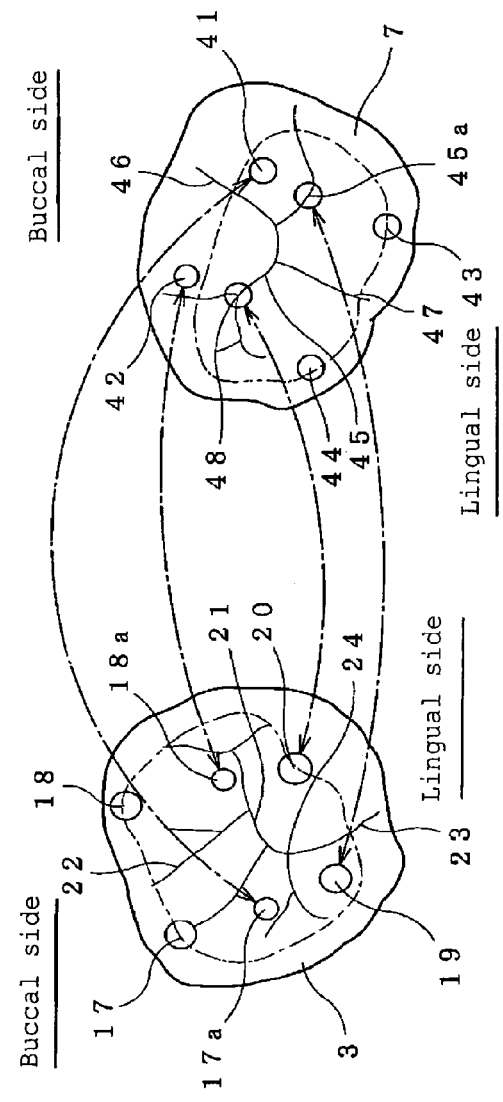

As shown in FIG. 3 (A), the second premolar teeth 2, 6 are configured such that the lingual cusp 14 of the maxillary second premolar tooth 2 is engaged with (contacts with) the lingual side fossa 40 formed on the central groove 39 of the mandibular second premolar tooth 6. In this engagement, since the cusp top of the lingual cusp 14 is fitted with the deep fossa 40 on the central groove 39, the mutual members are not free to move, and are fixed in the place. Because of this portion, the upper and lower jaws are fixed and a stable position relation is maintained. That is, the position is determined in the relation of the artificial molar teeth 1 to 4 and 5 to 8 of the upper and lower jaws.

The second premolar teeth 2, 6 are configured such that the buccal cusp 37 of the mandibular second premolar tooth 6 is engaged with a specified position on a sub-groove 15a branched from the central groove 15 of the maxillary second premolar tooth 2. In this engagement, since the cusp top of the buccal cusp 37 is fitted with the valley portion of the central groove 15, and hence it is free to move along the central groove 15 different from the case of the engagement of the cusp top with the fossa.

That is, the second premolar teeth 2, 6 are made such that the lingual cusp 14 of the maxillary second premolar tooth 2 and the fossa 40 of the mandibular second premolar tooth 6, and the buccal cusp 37 of the mandibular second premolar tooth 6 and the central groove 15 of the maxillary second premolar tooth 2 may correspond to each other. The second premolar teeth 2, 6 are also provided with the buccal cusp 13 of the maxillary second premolar tooth 2 and the lingual cusp 38 of the mandibular second premolar tooth 6, in addition to the cusps 14, 37 engaged with the fossa 40 or the groove 15. Each cusp top of these cusps 13, 38 does not engage or contact with any one of the antagonist 6, 2.

As shown in FIG. 3 (B), the first molar teeth 3, 7 are configured such that the distal lingual cusp 20 of the maxillary first molar tooth 3 as a crushing cusp is engaged with the fossa 48 on the central groove 45 of the mandibular first molar tooth 7. In this engagement, similarly to the second premolar teeth 2, 6, the cusp top of the distal lingual cusp 20 is fitted with the deep fossa 48 on the central groove 45, and the mutual members are not free to move, and are fixed in the place. Because of this portion, the upper and lower jaws are fixed and a stable position relation is maintained. That is, the position is determined in the relation of the artificial molar teeth 1 to 4 and 5 to 8 of the upper and lower jaws.

The first molar teeth 3, 7 are configured such that the mesial lingual cusp 19 of the maxillary first molar tooth 3 is engaged with a mesial groove 45a extending toward the mesial side of the central groove 45 of the mandibular first molar tooth 7. In this engagement, similarly to the second premolar teeth 2, 6, since the cusp top of the mesial lingual cusp 19 is fitted with the valley portion of the central groove 45, it is free to move along the central groove 45.

Further, the first molar teeth 3, 7 are configured such that the mesial buccal cusp 41 of the mandibular first molar tooth 7 contacts with a contour 17a which is the bulged portion of the mesial buccal cusp 17 of the maxillary first molar tooth 3. This contact position is a portion determined when the position relation of the other cusp and the fossa or the cusp and the groove is determined, and it is free to move by adjustment. That is, it is free to be determined by the relation of the other portions of the maxillary and mandibular artificial molar teeth 1 to 4, 5 to 8. Because of this portion, the upper and lower jaws are determined, and a stable position relation is maintained.

Further, the first molar teeth 3, 7 are configured such that the distal buccal cusp 42 of the mandibular first molar tooth 7 contacts with a contour 18a which is the bulged portion of the distal buccal cusp 18 of the maxillary first molar tooth 3. This contact position is a portion determined when the portion relation of the other cusp and the fossa or the cusp and the groove is determined, similarly to the case above, and it is free to move by adjustment. That is, it is free to determine by the relation of the other portions of the maxillary and mandibular artificial molar teeth 1 to 4, 5 to 8. Because of this portion, the upper and lower jaws are determined, and a stable position relation is maintained.

That is, the first molar teeth 3, 7 are fabricated such that the distal lingual cusp 20 of the maxillary first molar tooth 3 and the fossa 48 of the mandibular first molar tooth 7, the mesial lingual cusp 19 of the maxillary first molar tooth 3 and the central groove 45 of the mandibular first molar tooth 7, the mesial buccal cusp 41 of the mandibular first molar tooth 7 and the bulk portion 17a of the maxillary first molar tooth 3, and the distal buccal cusp 42 of the mandibular first molar tooth 7 and the bulk portion 18a of the maxillary first molar tooth 3 may correspond to each other. The first molar teeth 3, 7 are also provided with the buccal cusps 17, 18 of the maxillary first molar tooth 3 and the lingual cusps 43, 44 of the mandibular first molar tooth 7, in addition to the cusps 20, 19 engaged with the fossa 48 or the groove 45, and the cusps 41, 42 contacting with the bulk portions 17a. 18a. Each cusp top of these cusps 17, 18, 43, 44 does not engage or contact with any one of the antagonist 7, 3.

When arranging the maxillary molar teeth 1 to 4 and the mandibular molar teeth 5 to 8 having such configuration in each base 57, 58, for example, the maxillary first premolar tooth 1 is arranged in the maxillary base 57, and then the mandibular first premolar tooth 5 is arranged in the mandibular base 58. At this time, these first premolar teeth 1, 5 are occluded, and the lingual cusp 10 of the maxillary first premolar tooth 1 is engaged with the fossa 36 of the mandibular first premolar tooth 5. By rotating the tooth about the center of this engagement point, it is adjusted such that the buccal cusp 33 of the mandibular first premolar tooth 5 may be engaged with the central groove 11 of the maxillary first premolar tooth 1.

Next, the maxillary second premolar tooth 2 is arranged in the maxillary base 57. At this time, it is arranged such that one point of the outer circumference contacts with the previously arranged maxillary first premolar tooth 1. Then, the mandibular second premolar tooth 6 is arranged in the mandibular base 58. At this time, similarly to the maxillary second premolar tooth 2, it is arranged such that one point of the outer circumference contacts with the previously arranged mandibular first premolar tooth 5. Further, by occlusion of the second premolar teeth 2, 6 of the upper and lower jaws, the lingual cusp 14 of the maxillary second premolar tooth 2 is engaged with the fossa 40 of the mandibular second premolar tooth 6. By rotating the tooth about the center of this engagement point, it is adjusted such that the buccal cusp 37 of the mandibular second premolar tooth 6 is engaged with the central groove 15 of the maxillary second premolar tooth 2.

Next, the maxillary first molar tooth 3 is arranged in the maxillary base 57. At this time, it is arranged such that one point of the outer circumference contacts with the previously arranged maxillary second premolar tooth 2. Then, the mandibular first molar tooth 7 is arranged in the mandibular base 58. At this time, similarly to the maxillary first molar tooth 3, it is arranged such that one point of the outer circumference contacts with the previously arranged mandibular second premolar tooth 6. Further, by occlusion of the first molar teeth 3, 7 of the upper and lower jaws, the distal lingual cusp 20 of the maxillary first molar tooth 3 is engaged with the fossa 48 of the mandibular first molar tooth 7. By rotating about the center of this engagement point, it is adjusted such that the mesial lingual cusp 19 of the mandibular first molar tooth 3 may be engaged with the central groove 45 of the mandibular first molar tooth 7. It is further adjusted such that each of the buccal cusps 41, 42 of the mandibular first molar tooth 7 contacts with each of the bulk portions 17a, 18a of the maxillary first molar tooth 3.

Finally, the maxillary second molar tooth 43 is arranged in the maxillary base 57. At this time, it is arranged such that one point of the outer circumference contacts with the previously arranged maxillary first molar tooth 3. Then, the mandibular second molar tooth 8 is arranged in the mandibular base 58. At this time, similarly to the maxillary second molar tooth 4, it is arranged such that one point of the outer circumference contacts with the previously arranged mandibular first premolar tooth 5. Further, by occlusion of the second molar teeth 4, 8 of the upper and lower jaws, the distal lingual cusp 28 of the maxillary second molar tooth 4 is engaged with the fossa 56 of the mandibular second molar tooth 8. By rotating the tooth about the center of this engagement point, it is adjusted such that the mesial lingual cusp 27 of the mandibular second molar tooth 4 is engaged with the central groove 53 of the mandibular second molar tooth 8. It is further adjusted such that the buccal cusps 49, 50 of the mandibular second molar tooth 8 contact with the bulk portions of the maxillary second molar tooth 4.

In this way, in the artificial molar teeth 1 to 8 of the embodiment, only with a fine adjustment by rotation while the cusps of the specified teeth 1 to 3 are engaged with the fossae of the antagonist 5 to 8, the other cusps may be easily engaged with the grooves of the antagonist, and the teeth can be arranged by adjusting to specified positions. That is, when arranging the artificial molar teeth 1 to 8, high precision is not required in the position of arrangement. Hence, when making according to the oral cavity environment of a patient at the time of manufacture, the upper and lower teeth 1 to 4, 5 to 8 can be arranged at specified positions without requiring advanced techniques or experiences. When molding the artificial molar teeth 1 to 8, high precision is not also demanded, and the artificial teeth can be arranged in spite of some deformations. As a result, the manufacturing cost of the artificial molar teeth 1 to 8 can be saved significantly. Further, even if deformation due to polymerization shrinkage of the bases 57, 58 is generated, it is easy to repair.

Further, the oral cavity environment of the patient varies significantly in individual patients, and the oral cavity, and the height and angle of an alveolar ridge are varied in the edentulous jaw. Even in such clinical cases, the artificial teeth can be arranged easily in a short time, and the oral cavity environment can be reproduced. Further, if remaining teeth are present, it has been difficult to arrange the artificial molar teeth 1 to 8 at specified positions, but the fitting positions of the upper and lower jaws can be adjusted easily. As a result, after mounting of a dental prosthetic appliance, the oral cavity is enhanced aesthetically. Moreover, since the cusp to be engaged with the fossa is a crushing cusp, in addition to cutting function, grinding function can be added, and therefore chewing can be carried out easily.

The artificial molar teeth of the invention is not limited to the configurations shown in the embodiment, but may be modified variously.

For example, in the embodiment, the cusps of the maxillary molar teeth 1 to 4 and the fossae of the mandibular molar teeth 5 to 8 are engaged with each other, but it may be configured such that the cusps of the mandibular molar teeth 5 to 8 are engaged with the fossae of the maxillary molar teeth 1 to 4. Similarly, in the embodiment, the cusps of the maxillary molar teeth 1 to 4 and the grooves of the mandibular molar teeth 5 to 8 are engaged with each other, but it may be configured such that the cusps of the mandibular molar teeth 5 to 8 are engaged with the grooves of the maxillary molar teeth 1 to 4. Of course, in the adjacent teeth 1 to 4, 5 to 8, the cusps engaged with the fossae or grooves may be divided into upper and lower portions. That is, in the first premolar teeth 1, 5, the cusp of the maxillary first premolar tooth 1 may be engaged with the fossa of the mandibular first premolar tooth 5, and in the second premolar teeth 2, 6, the cusp of the mandibular second premolar tooth 6 may be engaged with the fossa of the maxillary second premolar tooth 2.

In the molar teeth 3, 4, 7, 8, the cusps to be engaged with the fossae and the grooves are the same maxillary molar teeth 1 to 4, but of the maxillary molar teeth 1 to 4 and the mandibular molar teeth 5 to 8, it may be configured such that one cusp is engaged with the other fossa, and the other cusp maybe engaged with one groove. It may be configured such that one cusp is shown to be engaged with the groove, but two or more cusps may be engaged with the individual grooves.

What is claimed is:

1. A method for positioning artificial teeth, the method comprising:
arranging a first molar tooth on a first base, the first molar tooth having a lingual cusp and a central groove;
arranging a second molar tooth on a second base, the second molar tooth having a fossa and a buccal cusp;
adjusting the relative position of the first molar tooth and the second molar tooth, so as to present the first molar tooth and the second molar tooth in a central occlusal position, by:
(i) engaging the lingual cusp of the first molar tooth with the fossa of the second molar tooth such that a fossa-cusp engagement is established at a fossa-cusp engagement point; and
(ii) rotating at least one of the first molar tooth and the second molar tooth about the fossa-cusp engagement point until the buccal cusp of the second molar tooth engages the central groove of the first molar tooth,
wherein one of the first molar tooth and the second molar tooth is a maxillary molar tooth and the other of the first molar tooth and the second molar tooth is a mandibular molar tooth.

2. The method of claim 1, wherein the first molar tooth is one of a first maxillary premolar tooth, a second maxillary premolar tooth, a first maxillary molar tooth, and a second maxillary molar tooth, and
wherein the second molar tooth is a corresponding mandibular tooth.

3. The method of claim 1, wherein the first molar tooth is one of a first mandibular premolar tooth, a second mandibular premolar tooth, a first mandibular molar tooth, and a second mandibular molar tooth, and
wherein the second molar tooth is a corresponding maxillary tooth.

4. The method of claim 1, wherein the first molar tooth includes a contour of a bulged portion of a mesial buccal cusp and a contour of a bulged portion of a distal buccal cusp,
wherein the second tooth further has a mesial buccal cusp and a distal buccal cusp, and
wherein said adjusting the relative position of the first molar tooth and the second molar tooth includes:
(i) contacting the mesial buccal cusp of the second molar tooth with the contour of the bulged portion of the mesial buccal cusp first molar tooth; and
(ii) contacting the distal buccal cusp of the second molar tooth with the contour of the bulged portion of the distal buccal cusp of the first molar tooth.

5. The method of claim 4, wherein the first molar tooth is one of a first maxillary premolar tooth, a second maxillary premolar tooth, a first maxillary molar tooth, and a second maxillary molar tooth, and
wherein the second molar tooth is a corresponding mandibular tooth.

6. The method of claim 4, wherein the first molar tooth is one of a first mandibular premolar tooth, a second mandibular premolar tooth, a first mandibular molar tooth, and a second mandibular molar tooth, and
wherein the second molar tooth is a corresponding maxillary tooth.

7. A method for positioning artificial teeth, the method comprising:
arranging a first molar tooth on a first base, the first molar tooth having a lingual cusp and a central groove;
arranging a second molar tooth on a second base, the second molar tooth having a fossa and a buccal cusp;
adjusting the relative position of the first molar tooth and the second molar tooth, so as to present the first molar tooth and the second molar tooth in a central occlusal position, by:
(i) engaging the lingual cusp of the first molar tooth with the fossa of the second molar tooth such that a fossa-cusp engagement is established at a fossa-cusp engagement point; and (ii) rotating at least one of the first molar tooth and the second molar tooth about the fossa-cusp engagement point until the buccal cusp of the second molar tooth engages the central groove of the first molar tooth;

arranging a third molar tooth on the first base, the third molar tooth having a lingual cusp and a central groove;

arranging a fourth molar tooth on the second base, the fourth molar tooth having a fossa and a buccal cusp;

adjusting the relative position of the third molar tooth and the fourth molar tooth, so as to present the first molar tooth and the second molar tooth in a central occlusal position, by:

(iii) engaging the lingual cusp of the third molar tooth with the fossa of the fourth molar tooth such that a fossa-cusp engagement is established at a fossa-cusp engagement point; and (iv) rotating at least one of the third molar tooth and the fourth molar tooth about the fossa-cusp engagement point until the buccal cusp of the fourth molar tooth engages the central groove of the third molar tooth;

wherein one of the first molar tooth and the second molar tooth is a maxillary molar tooth and the other of the first molar tooth and the second molar tooth is a mandibular molar tooth, and wherein one of the third molar tooth and the fourth molar tooth is a maxillary molar tooth and the other of the third molar tooth and the fourth molar tooth is a mandibular molar tooth.

8. The method of claim 7, wherein the first molar tooth is one of a first maxillary premolar tooth and a second maxillary premolar tooth, and the second molar tooth is a corresponding mandibular tooth, wherein the third molar tooth is one of a first maxillary molar tooth and a second maxillary molar tooth, and the fourth molar tooth is a corresponding mandibular tooth.

9. The method of claim 7, wherein the first molar tooth is one of a first mandibular premolar tooth and a second mandibular premolar tooth, and the second molar tooth is a corresponding maxillary tooth, wherein the third molar tooth is one of a first mandibular molar tooth and a second mandibular molar tooth, and the fourth molar tooth is a corresponding maxillary tooth.

10. The method of claim 7, wherein the first molar tooth includes a contour of a bulged portion of a mesial buccal cusp and a contour of a bulged portion of a distal buccal cusp, wherein the second tooth further has a mesial buccal cusp and a distal buccal cusp, and wherein said adjusting the relative position of the first molar tooth and the second molar tooth includes:

(iii) contacting the mesial buccal cusp of the second molar tooth with the contour of the bulged portion of the mesial buccal cusp first molar tooth; and (iv) contacting the distal buccal cusp of the second molar tooth with the contour of the bulged portion of the distal buccal cusp of the first molar tooth.

11. The method of claim 10, wherein the first molar tooth is one of a first maxillary premolar tooth and a second maxillary premolar tooth, and the second molar tooth is a corresponding mandibular tooth, wherein the third molar tooth is one of a first maxillary molar tooth and a second maxillary molar tooth, and the fourth molar tooth is a corresponding mandibular tooth.

12. The method of claim 10, wherein the first molar tooth is one of a first mandibular premolar tooth and a second mandibular premolar tooth, and the second molar tooth is a corresponding maxillary tooth, wherein the third molar tooth is one of a first mandibular molar tooth and a second mandibular molar tooth, and the fourth molar tooth is a corresponding maxillary tooth.

\* \* \* \* \*